US011141296B2

(12) United States Patent
Thompson

(10) Patent No.: US 11,141,296 B2
(45) Date of Patent: Oct. 12, 2021

(54) RADIOPAQUE ENHANCED COBALT ALLOY FOR STENTS

(71) Applicant: Medtronic Vascular, Inc., Santa Rosa, CA (US)

(72) Inventor: Dustin Thompson, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 456 days.

(21) Appl. No.: 15/421,632

(22) Filed: Feb. 1, 2017

(65) Prior Publication Data

US 2017/0135831 A1 May 18, 2017

Related U.S. Application Data

(62) Division of application No. 13/771,907, filed on Feb. 20, 2013, now Pat. No. 9,592,135.

(60) Provisional application No. 61/639,021, filed on Apr. 26, 2012.

(51) Int. Cl.
| *C22C 19/07* | (2006.01) |
| *A61F 2/82* | (2013.01) |
| *A61F 2/915* | (2013.01) |
| *A61L 31/18* | (2006.01) |
| *A61L 31/02* | (2006.01) |
| *C22F 1/10* | (2006.01) |

(52) U.S. Cl.
CPC .............. *A61F 2/915* (2013.01); *A61F 2/82* (2013.01); *A61L 31/022* (2013.01); *A61L 31/18* (2013.01); *C22C 19/07* (2013.01); *A61F 2002/91558* (2013.01); *A61F 2210/0076* (2013.01); *A61F 2250/0098* (2013.01)

(58) Field of Classification Search
CPC .......... A61F 2/82; A64L 31/18; A64L 31/022; C22C 19/07; C22C 19/00; C22C 19/002; C22C 19/005; C22C 19/007; C22F 1/10
USPC ........................................ 148/313, 408, 425
See application file for complete search history.

(56) References Cited

U.S. PATENT DOCUMENTS

| 5,858,556 A | 1/1999 | Eckert et al. |
| 5,983,951 A | 11/1999 | Tanguchi et al. |
| 6,027,528 A | 2/2000 | Tomonto et al. |
| 6,248,190 B1 | 6/2001 | Stinson |
| (Continued) | | |

FOREIGN PATENT DOCUMENTS

| JP | 2000104141 | 4/2000 |
| JP | 2003166026 | 6/2003 |
| (Continued) | | |

OTHER PUBLICATIONS

1st Japanese Office Action, Appln No. 2015-508950, dated Dec. 14, 2016.

*Primary Examiner* — Lois L Zheng

(57) ABSTRACT

A stent is formed of at least a cobalt-based alloy. The cobalt-based alloy may include 10-35 weight % metal member selected from the group consisting of platinum (Pt), gold (Au), iridium (Ir), osmium (Os), rhenium (Re), tungsten (W), palladium (Pd), tantalum (Ta), and combinations thereof; 16-21 weight % chromium (Cr); 9-12 weight % molybdenum (Mo); 0-25 weight % nickel (Ni); and balance cobalt (Co). The cobalt-based alloy may be a thin outer shell of a hollow stent. The cobalt-based alloy may be used to form at least one of an inner core and an outer shell of a core-shell structure of a stent. The cobalt-based alloy may be used to form an end of a wire for forming a stent.

9 Claims, 8 Drawing Sheets

(56) References Cited

U.S. PATENT DOCUMENTS

| | | |
|---|---|---|
| 6,419,693 B1 | 7/2002 | Fariabi |
| 6,497,709 B1 | 12/2002 | Heath |
| 6,527,802 B1 | 3/2003 | Mayer |
| 6,746,478 B2 | 6/2004 | Jayaraman |
| 7,250,058 B1 | 7/2007 | Pacetti et al. |
| 7,329,383 B2 | 2/2008 | Stinson |
| 7,445,749 B2 | 11/2008 | Craig |
| 7,540,997 B2 | 6/2009 | Stinson |
| 7,780,798 B2 | 8/2010 | Stinson et al. |
| 2003/0018380 A1 | 1/2003 | Craig et al. |
| 2003/0194343 A1 | 10/2003 | Craig |
| 2003/0195609 A1 | 10/2003 | Berenstein et al. |
| 2004/0106982 A1 | 6/2004 | Jalisi |
| 2004/0129347 A1 | 7/2004 | Craig |
| 2005/0145508 A1 | 7/2005 | Larsen et al. |
| 2006/0147334 A1 | 7/2006 | Cascone |
| 2007/0135734 A1 | 6/2007 | Reynolds et al. |
| 2007/189917 A1 | 8/2007 | Stinson |
| 2009/0292351 A1 | 11/2009 | McClain et al. |
| 2010/0004726 A1 | 1/2010 | Hancock et al. |
| 2010/0145268 A1 | 6/2010 | Stinson |
| 2011/0257732 A1 | 10/2011 | McClain et al. |
| 2012/0067103 A1 | 3/2012 | Bienvenu et al. |
| 2012/0123525 A1 | 5/2012 | Kramer-Brown et al. |
| 2013/0073028 A1 | 3/2013 | Chiba |
| 2013/0226281 A1 | 8/2013 | Chiba et al. |

FOREIGN PATENT DOCUMENTS

| | | |
|---|---|---|
| WO | 95/30384 A2 | 11/1995 |
| WO | WO200172349 | 10/2001 |
| WO | WO2005039663 | 5/2005 |
| WO | 2006/022754 A2 | 3/2006 |
| WO | WO2008024537 | 2/2008 |
| WO | WO2012068358 | 5/2012 |

RADIOPAQUE ENHANCED COBALT ALLOY FOR STENTS

CROSS-REFERENCE TO RELATED APPLICATIONS

This application is a Division of and claims the benefit of U.S. patent application Ser. No. 13/771,907, filed Feb. 20, 2013, now allowed, which claims the benefit of priority from U.S. Provisional Patent Application Ser. No. 61/639,021, filed on Apr. 26, 2012. The disclosures of which are herein incorporated herein by reference in their entirety.

FIELD

The present invention is related to cobalt-based alloys that are used to manufacture implantable medical devices, such as stents.

BACKGROUND

A stent is typically a hollow, generally cylindrical device that is deployed in a body lumen from a radially contracted configuration into a radially expanded configuration, which allows it to contact and support a vessel wall. A plastically deformable stent may be implanted during an angioplasty procedure by using a balloon catheter bearing a compressed or "crimped" stent, which has been loaded onto the balloon. The stent radially expands as the balloon is inflated, forcing the stent into contact with the body lumen, thereby forming a support for the vessel wall. Deployment is effected after the stent has been introduced percutaneously, transported transluminally, and positioned at a desired location by means of the balloon catheter.

Stents may be formed from wire(s) or strip(s) of material, may be cut from a tube, or may be cut from a sheet of material and then rolled into a tube-like structure. As new generations of stents become thinner in strut dimension/thickness, many metal alloys that have historically been used for stents may not have enough radio-density, or radiopacity, for appropriate visualization under fluoroscopy or x-ray, which may be used to visualize the location of the stent as it is transported transluminally.

SUMMARY

It is desirable to develop materials for implantable medical devices, such as stents, to provide enhanced radiopacity, while retaining or improving mechanical properties including, but not limited to, mechanical strength, toughness, durability, flexibility, deliverability, minimal recoil, ductility, and/or corrosion resistance, of materials that are currently used for such implantable medical devices.

According to an aspect of embodiments of the present invention, there is provided a stent that includes a cobalt-based alloy. The cobalt-based alloy includes 10-35 weight % material selected from the group consisting of platinum (Pt), gold (Au), iridium (Ir), osmium (Os), rhenium (Re), tungsten (W), palladium (Pd), tantalum (Ta), and combinations thereof; 16-21 weight % chromium (Cr); 9-12 weight % molybdenum (Mo); 0-25 weight % nickel (Ni); and balance cobalt (Co).

According to an aspect of embodiments of the present invention, there is provided a stent that includes a cobalt-based alloy, wherein the cobalt-based alloy is free of nickel (Ni). The cobalt-based alloy includes 10-35 weight % metal member selected from the group consisting of platinum (Pt), gold (Au), iridium (Ir), osmium (Os), rhenium (Re), tungsten (W), palladium (Pd), tantalum (Ta), and combinations thereof; 16-21 weight % chromium (Cr); 0-12 weight % molybdenum (Mo); 0-3 weight % iron (Fe); and balance cobalt (Co).

According to an aspect of embodiments of the present invention, there is provided a stent that includes a cobalt-based alloy, wherein the cobalt-based alloy is free of molybdenum (Mo). The cobalt-based alloy includes 10-35 weight % metal member selected from the group consisting of platinum (Pt), gold (Au), iridium (Ir), osmium (Os), rhenium (Re), tungsten (W), palladium (Pd), tantalum (Ta), and combinations thereof; 20-24 weight % chromium (Cr); 0-12 weight % nickel (Ni); 0-3 weight % iron (Fe); and balance cobalt (Co).

According to an aspect of embodiments of the present invention, there is provided a stent that includes a plurality of struts formed by a wire. The wire includes an outer shell substantially surrounding an inner core, wherein at least one of the outer shell and the inner core comprises a metal member selected from the group consisting of platinum (Pt), gold (Au), iridium (Ir), osmium (Os), rhenium (Re), tungsten (W), palladium (Pd), tantalum (Ta), and combinations thereof, and wherein at least one end of the wire is formed of a cobalt-based alloy. The cobalt-based alloy includes 10-35 weight % the metal member; 16-21 weight % chromium (Cr); 0-12 weight % molybdenum (Mo); 0-25 weight % nickel (Ni); 0-3 weight % iron (Fe); and balance cobalt (Co).

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Figure 1:
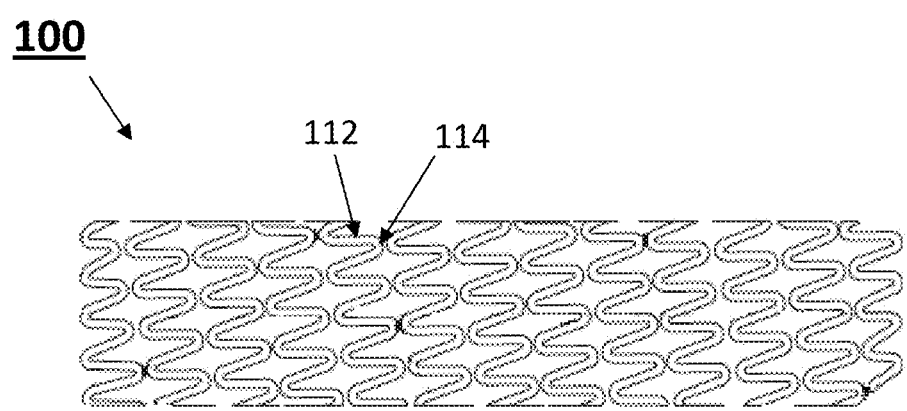
FIG. 1 depicts a stent having struts and crowns in accordance with various embodiments of the present invention.

Embodiments of the present invention are directed to an inventive Co-based alloy to achieve enhanced radiopacity, while retaining or improving other properties, such as mechanical properties.

According to embodiments of the invention the Co-based alloys may include at least one metal element that has a density and/or atomic number that is greater than the other metal elements in commercially available Co-based alloys. Examples of commercially available Co-based alloys include those having trade names of MP35N, MP35N LT, L-605, Haynes 188, and/or other Co-containing alloys known in the art. For example, MP35N is generally known to have a typical composition of about 35% Ni, about 35% Co, about 20% Cr, and about 10% Mo (35Co-35Ni-20Cr-10Mo) by weight; MP35N LT may have a typical composition of 33-37% Ni, 19-21% Cr, 9-10.5% Mo, and balance Co by weight measured according to ASTM F562; and L-605 may have a typical composition of about 9-11% Ni, 19-21% Cr, 14-16% W, and balance Co by weight. To some extent, MP35N LT may be considered as an alternative to MP35N. Although both of these alloys have about the same composition (35Co-35Ni-20Cr-10Mo), MP35N contains about 1% titanium by weight, while the MP35N LT (low titanium) composition contains only 0.01% titanium by weight. The reduction in titanium content may cause reduced inclusion sizes and distribution, better surface finish, and greatly improved fatigue life.

As noted above, according to embodiments of the invention, at least one metal element that has a density and/or atomic number that is greater than the other metal elements in commercially available Co-based alloys, such as the Co-based alloys listed above, may have density of about 12 g/cm$^3$ or higher. For convenience, the term "dense metal member" or "elemental dense metal" will be used to describe such an element, and may include, without limitation, platinum (Pt), gold (Au), iridium (Ir), osmium (Os), rhenium (Re), tungsten (W), palladium (Pd), and/or tantalum (Ta). In some embodiments, the dense metal member may be Pt or Pt-containing alloy such as PtIr. In other embodiments, the dense metal member may be formed by elemental dense metal(s) other than Pt.

As compared to existing or conventional Co-based alloys, the Co-based alloys according to embodiments of the invention may have a composition that has a reduced content of nickel (Ni) and/or other metals, while the content of the remaining metal(s) in the existing Co-based alloys may or may not be reduced. In an embodiment, Ni and/or other metals in the existing Co-based alloys may be at least partially replaced by the disclosed dense metal member, and/or their alloys. In an embodiment, the disclosed Co-based alloys may be formed by balancing dense metal member(s) with the existing Co-based alloys, wherein the material ratio between metals in the existing Co-based alloys is maintained.

In a specific example, Ni may be completely removed from existing Co-based alloys while Pt with a higher density may be included in the Co-based alloys. Both Pt and Ni are transition metals with a face cubic centered (FCC) structure known to provide ductility without affecting properties or characteristics of the final alloy and to be an austenite stabilizer. In another example, Pt may be added into, e.g., melted into MP35N or MP35N LT, without affecting the corrosion resistance of the MP35N.

In a first exemplary embodiment, the cobalt-based alloy used to form a stent may include, but not be limited to,
- 10-35 weight %, for example, 10-35, 20-35, or about 35 weight % dense metal member;
- 16-21 weight %, for example, 19-21 weight % chromium (Cr);
- 9-12 weight %, for example, 9-10.5 weight % molybdenum (Mo);
- 0-25 weight %, for example, 10-18 weight % nickel (Ni); and balance cobalt (Co).

In an embodiment, the cobalt-based alloy may further include one or more of iron (Fe), boron (B), carbon (C), manganese (Mn), phosphorous (P), silicon (Si), titanium (Ti), sulfur (S), and/or combinations thereof, for example, by weight:
- 0-3.0% or 0-1.0% or about 1% iron (Fe);
- 0-0.015% or about 0.010 or 0.015% boron (B);
- 0-0.15% or 0-0.025% or about 0.025% carbon (C);
- 0-1.5% or 0-0.15% or about 0.15% manganese (Mn);
- 0-0.04% or 0-0.015% or about 0.015% phosphorous (P);
- 0-1.0% or 0-0.15% or about 0.15% silicon (Si);
- 0-1% or 0-1% or about 0.01% titanium (Ti); and
- 0-0.03% or 0-0.01% or about 0.01% sulfur (S).

In a second exemplary embodiment, the cobalt-based alloy used to form a stent may be free of nickel (Ni). For example, the disclosed cobalt-based alloys may include, but not be limited to,
- 10-35 weight %, for example, 10-35, 20-35, or 35 weight % dense metal member;
- 16-21 weight %, for example, 19-21 weight % chromium (Cr);
- 0-12 weight %, for example, 9-12 or 9-10.5 weight % molybdenum (Mo);
- 0-3 weight % iron (Fe); and balance cobalt (Co).

In an embodiment, the cobalt-based alloy may further include one or more of, by weight,
- 0-0.15% carbon (C);
- 0-1.5% manganese (Mn);
- 0-0.04% phosphorous (P);
- 0-1.0% silicon (Si);
- 0-1% titanium (Ti); and
- 0-0.03% sulfur (S).

In an embodiment, the cobalt-based alloy that is free of nickel (Ni) may be further free of molybdenum (Mo), boron (B), titanium (Ti), and/or their combinations. In this embodiment, the cobalt-based alloy may be formed of, for example, about 15 weight % tungsten (W) and 10-12 weight % platinum (Pt);
- about 20 weight % chromium (Cr);
- 0-0.15 weight % carbon (C);
- 0-3 weight % iron (Fe);
- about 1.5 weight % manganese (Mn);
- 0-0.04 weight % phosphorous (P);
- 0-1.0 weight % silicon (Si);
- 0-0.03 weight % sulfur (S); and
- balance cobalt (Co).

In a third exemplary embodiment, the cobalt-based alloy used to form a stent may include, without limitation:
- 10-35 weight % dense metal member;
- 16-21 weight % chromium (Cr);
- 0-12 weight % molybdenum (Mo);

0-25 weight % nickel (Ni);
0-3 weight % iron (Fe); and
balance cobalt (Co).

In a fourth exemplary embodiment, the cobalt-based alloy used to form a stent may include, without limitation:

10-35 weight % metal member selected from the group consisting of platinum (Pt), gold (Au), iridium (Ir), osmium (Os), rhenium (Re), tungsten (W), palladium (Pd), tantalum (Ta), and combinations thereof;
20-24 weight % chromium (Cr);
0-12 weight % nickel (Ni);
0-3 weight % iron (Fe); and
balance cobalt (Co).

In an embodiment, the cobalt-based alloy is free of molybdenum (Mo) and may be formed of:

about 14 weight % tungsten (W) and 10-14 weight % platinum (Pt);
about 22 weight % chromium (Cr);
8-12 weight % nickel (Ni)
0-0.15 weight % carbon (C);
0-3 weight % iron (Fe);
about 1.5 weight % manganese (Mn);
0-1.0 weight % silicon (Si);
0-0.03 weight % lanthanum (La); and
balance cobalt (Co).

The Co-based alloys disclosed herein may be used to form the wires, sheets, and tubes from which stents with desired properties, as described herein.

In an embodiment, a stent may be formed from a wire that includes a core-shell structure having an outer shell substantially surrounding an inner core. One or both of the outer shell and the inner core may be formed of the cobalt-based alloy. For example, one of the outer shell and the inner core may be formed of the cobalt-based alloy and the other thereof may be formed of a metal member. The metal member may be any metal for providing additional properties as desired, and/or may be a dense metal member for providing improved radiopaque and/or mechanical properties. In an embodiment, the inner core may be hollow, while the outer shell may be formed of the disclosed cobalt-based alloys and may be thin with desired properties. Due to use of the disclosed Co-based alloys, thin struts with minimal recoil may also be achieved.

In exemplary embodiments in which the stent is formed by a wire that includes a core-shell structure, at least one of the outer shell and the inner core of the wire may be formed of a material including at least a dense metal member to provide the stent with at least one end formed of the cobalt-based alloys in accordance with embodiments of the invention.

FIG. 1 depicts a stent 100 according to an embodiment of the invention that includes a plurality of struts 112 and a plurality of crowns or turns 114, with each crown or turn 114 connecting a pair of adjacent struts 112. The stent 100 may be formed from a tube or wire using methods known in the art, and the tube or wire used to form the stent 100 may be made from materials in accordance with embodiments of the invention. For example, if a tube is used to form a stent, the tube may be cut with a laser or etched with the pattern of the stent by known methods. If a wire is used to form a stent, the wire may be formed into a generally sinusoidal waveform, and wrapped around a mandrel or rod. Select neighboring crowns may be fused together, and the ends of the wire may be cut by a laser where the stent terminates.

Figure 2A:
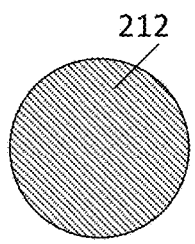
FIGS. 2A and 2B depict cross-sections of various exemplary struts of stents in accordance with various embodiments of the present invention.
Figure 2B:
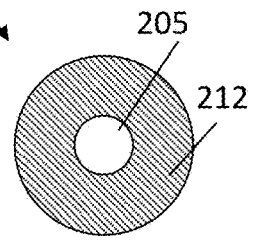

FIGS. 2A and 2B depict cross-sections of struts of stents 200A, 200B, respectively, in accordance with embodiments of the invention.

In FIG. 2A, a Co-based alloy 212 as disclosed herein may be used to form a wire used to form the struts of stent 200A having the desired radiopacity, mechanical properties, and/or other properties.

In FIG. 2B, the struts of stent 200B may be formed from a wire that includes an outer shell formed of the disclosed Co-based alloy 212. The outer shell may substantially surround an inner core, which is a hollow inner core 205 in this embodiment, forming an open lumen. In embodiments, the outer shell may be thin having a thickness of about 0.0010 inches or less or ranging from about 0.0005 to about 0.0020 inches due to use of the disclosed Co-based alloy 212 to sufficiently provide desired radiopacity and/or mechanical properties.

Figure 2C:
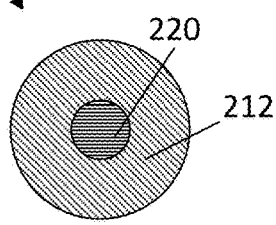
FIGS. 2C and 2D depict cross-sections of various exemplary composite struts of stents in accordance with various embodiments of the present invention.
Figure 2D:
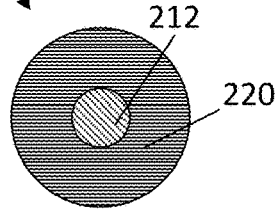

FIGS. 2C and 2D depict cross-sections of composite struts of stents 200C, 200D, respectively, in accordance with embodiments of the invention. Composite struts/stents may utilize different performance characteristics of individual materials to improve their overall performance.

In FIG. 2C, the exemplary struts of stent 200C may be formed to include an outer shell formed of the Co-based alloy 212 substantially surrounding an inner core formed by a metal member 220. The metal member 220 may be selected to provide desired properties. The metal member may include at least one metal and may be a metal alloy. The metal member 220 surrounded by the Co-based alloy 212 may or may not be a dense metal member. However, when a dense metal member is used for the metal member 220, the struts of stent 200C in FIG. 2C may have even further enhanced radiopacity while retaining (or improving) other properties, as disclosed herein.

In FIG. 2D, the metal member 220, such as a dense metal member, may be used as an outer shell substantially surrounding an inner core of the disclosed Co-based alloy 212 to form struts of stent 200D that has the desired radiopacity and other properties, depending the materials selected and used.

Figure 2E:
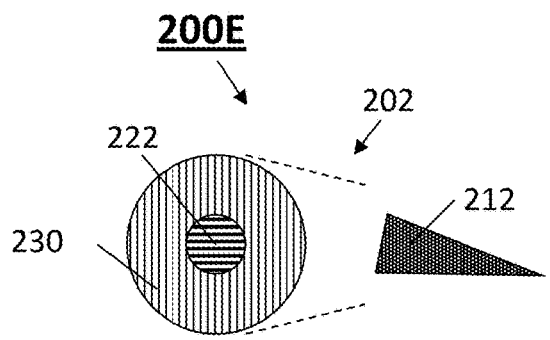
FIGS. 2E and 2F depict cross-sections and ends of exemplary wires used to form struts of stents in accordance with various embodiments of the present invention.
Figure 2F:
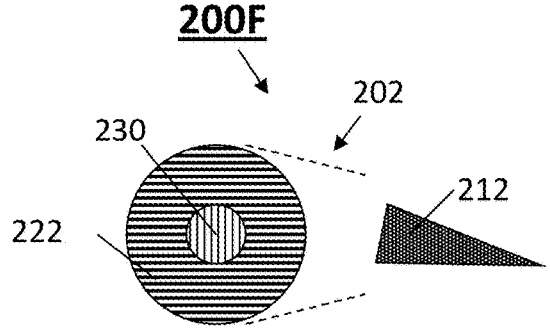

FIGS. 2E and 2F depict cross-sections and an end 202 of a wire used to form struts of stents 200E, 200F in accordance with various embodiments of the invention. For example, exemplary struts/stents may be formed by a wire and/or tube having an outer shell substantially surrounding an inner core such that a combination of materials of the outer shell and the inner core form a Co-based alloy with a dense metal member in accordance with embodiments of the invention at one or both ends of the wire/tube.

In FIG. 2E, the outer shell may be formed of any Co-based alloy 230 substantially surrounding an inner core formed of a dense metal member 222. The dense metal member 222 may be formed of at least one dense metal as disclosed herein. The Co-based alloy 230 may be any Co-based alloy as known in the art and/or may be a Co-based alloy containing at least one dense metal in accordance with embodiments of the invention.

For example, a composite wire with an outer shell of MP35N and an inner core of PtIr may be utilized to at least maintain all the mechanical performance comparable to a solid MP35N and further to add benefits of improved radiopacity from the core material. Specifically, during manufacturing, when using a laser to cut the ends of the wire where the stent terminates, the laser melts through both the MP35N and the core material, and the melting leaves a smooth tapered end to the wire. By melting through both materials of the outer shell and the inner core, the Co-based alloy 212 in accordance with embodiments of the invention may provide tapered ends of the wire.

In FIG. 2F, the composition wire may include an outer shell formed of a dense metal member 222 substantially surrounding a Co-based alloy 230 as an inner core to provide an end of the wire with desired properties to form a stent.

In embodiments, the dense metal member 222 may be about 20% to about 45% by weight of the total wire including the dense metal member 222 and the Co-based alloy 230 as depicted in FIGS. 2E and 2F. For example, in an embodiment, the dense metal member 222 of FIG. 2E may be an alloy of platinum (Pt) and iridium (Ir), the Co-based alloy 230 may be MP35N, and the diameter of the core of PtIr may be about 10-25% of the diameter of the wire. In an embodiment, the dense metal member 222 of FIG. 2E may be tantalum (Ta), the Co-based alloy 230 may be MP35N, and the diameter of the core of Ta may be about 10-30% of the diameter of the wire.

In an embodiment, the exemplary stents 200E, 200F may further include struts depicted in FIGS. 2A-2D with desired ends (see FIGS. 2E and 2F) of wires/stents formed of at least a Co-based alloy according to embodiments of the invention.

Although the cross-sections depicted in FIGS. 2A-2F are circular for illustration purposes, one of ordinary skill in the art would appreciate that other possible cross-sections, regular or irregular, including a triangle, a square, a rectangle, a polygon, an oval, etc., may be used for the disclosed alloys/wires/tubes/struts/stents. In addition, the core-shell structures shown in FIGS. 2B-2F may be formed coaxially or non-coaxially, while the outer shell and the inner core may have the same or different cross-sectional shapes.

The following examples are illustrative of embodiments of the invention and not intended to be limiting.

EXAMPLES

Co-based alloys with various exemplary compositions as disclosed herein were draw down to about 0.0034″ (0.086 mm) on spools and melted for analysis. Melt analysis was conducted with energy dispersive (ED)-XRF spectrometers, which include, for example, x-Ray generator, x-Ray tube, HV supply, vacuum system, pulse processor, Si (Li) detector, targets, PC, MCA, printer, etc., to provide a concentration measurement of each element in the Co-based alloy samples. As measured, the higher the intensity of the signal, the higher the concentration of an element in the Co-based alloy samples. Preliminary evaluations revealed desired mechanical strength and ductility when compared to conventionally utilized stainless steel alloys, Co-based alloys, or other alloys.

Example 1

Table I lists alloy compositions (in weight %) for a Co-based alloy in Example 1.

TABLE I

Co-Based Alloy including Ni

| Element | Wt. % |
|---|---|
| Boron (B) | 0.010 |
| Carbon (C) | ≤0.025 |
| Chromium (Cr) | 19.0-21.0 |
| Cobalt (Co) | Remainder |
| Iron (Fe) | ≤1.0 |
| Manganese (Mn) | ≤0.15 |
| Molybdenum (Mo) | 9.0-10.5 |

TABLE I-continued

Co-Based Alloy including Ni

| Element | Wt. % |
|---|---|
| Nickel (Ni) | 0.0-25.0 |
| Phosphorous (P) | ≤0.015 |
| Platinum (Pt) | 10.0-35.0 |
| Silicon (Si) | ≤0.15 |
| Sulfur (S) | ≤0.010 |
| Titanium (Ti) | ≤1.0 |

Example 2

Table II lists alloy compositions (in weight %) for a Co-based alloy in Example 2:

TABLE II

Co-Based Alloy without Ni

| Element | Wt. % |
|---|---|
| Carbon (C) | ≤0.15 |
| Chromium (Cr) | 20.0 |
| Cobalt (Co) | Remainder |
| Iron (Fe) | ≤3.0 |
| Manganese (Mn) | 1.5 |
| Tungsten (W) | 15 |
| Phosphorous (P) | ≤0.040 |
| Platinum (Pt) | 10.0-12 |
| Silicon (Si) | ≤1.0 |
| Sulfur (S) | ≤0.030 |

Example 3

Table III lists alloy compositions (in weight %) for a Co-based alloy in

Example 3

TABLE III

Co-Based Alloy including Ni

| Element | Wt. % |
|---|---|
| Boron (B) | 0.015 |
| Carbon (C) | 0.025 |
| Chromium (Cr) | 20 |
| Cobalt (Co) | Remainder |
| Iron (Fe) | 1 |
| Manganese (Mn) | 0.15 |
| Molybdenum (Mo) | 10 |
| Nickel (Ni) | 12 |
| Phosphorous (P) | 0.015 |
| Platinum (Pt) | 24 |
| Silicon (Si) | 0.15 |
| Sulfur (S) | 0.01 |
| Titanium (Ti) | 0.01 |

Example 4

Table IV lists alloy compositions (in weight %) for a Co-based alloy in Example 4:

TABLE IV

Co-Based Alloy without Mo

| Element | Wt. % |
|---|---|
| Carbon (C) | 0-0.15 |
| Chromium (Cr) | 22 |
| Cobalt (Co) | Remainder |
| Iron (Fe) | 0-3 |
| Lanthanum (La) | 0-0.03 |
| Manganese (Mn) | 1.5 |
| Nickel (Ni) | 8-12 |
| Platinum (Pt) | 10-14 |
| Silicon (Si) | 0-1.0 |
| Tungsten (W) | 14 |

Example 5

Table V lists alloy compositions (in weight %) for each of exemplary Co-based alloys M1a, M1b, M2a, and M2b, and a commercially available alloy MP35N LT:

TABLE V

Co-Based Alloys including Ni

| | Element wt-% | | Element wt-% (with Ta-core) | | ASTM F562 wt % |
|---|---|---|---|---|---|
| Element Samples | M1a | M1b | M2a | M2b | MP35N LT |
| Co | Balance | 35.2 | Balance | 34 | balance |
| Cr | 20 | 16.8 | 20 | 19 | 19-21 |
| Ni | 15 | 17.2 | 12 | 17 | 33-37 |
| Mo | 10 | 11.1 | 10 | 11 | 9-10.5 |
| Pt | 24 | 20.1 | 24 | 19.5 | n/a |

Specifically, Table V compares Co-based alloy samples M1a and M1b when used as a wire for forming struts of a stent, and Co-based alloy samples M2a and M2b when used to form an outer shell substantially surrounding an exemplary tantalum (Ta) inner core for forming a wire for forming struts of a stent. Table V also includes the commercial alloy MP35N LT having weight concentration of each element measured by ASTM F562. All of the above exemplary alloy compositions were formulated by mixing powders of the elements and melting the mixed powders.

Mechanical Properties

Figure 3:
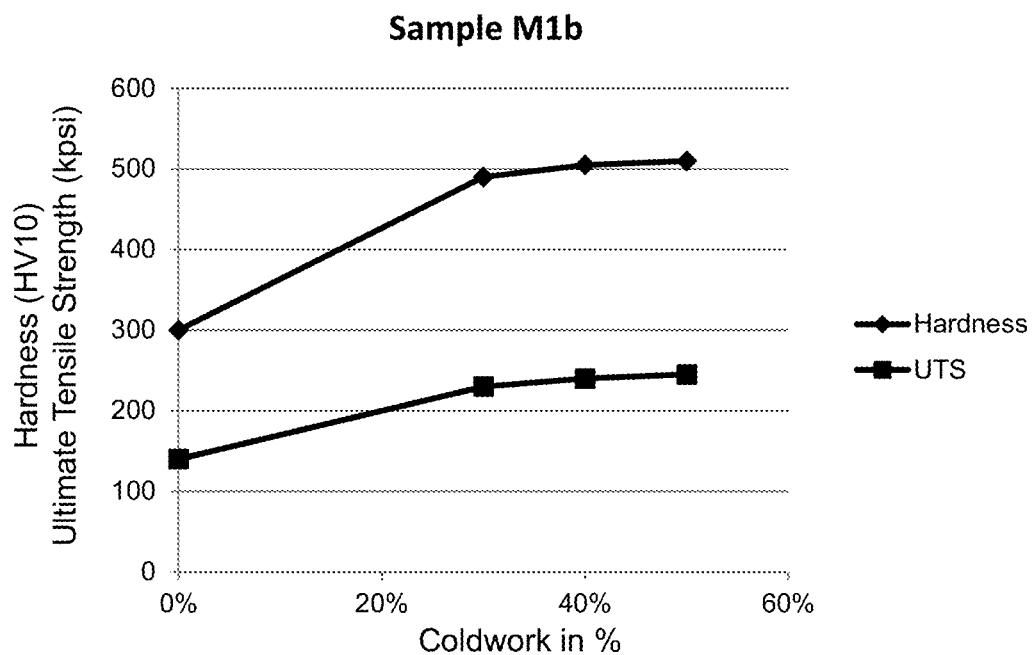
FIGS. 3 and 4 depict hardness and ultimate tensile strength (UTS) of exemplary Co-based alloys in accordance with various embodiments of the present invention.
Figure 4:
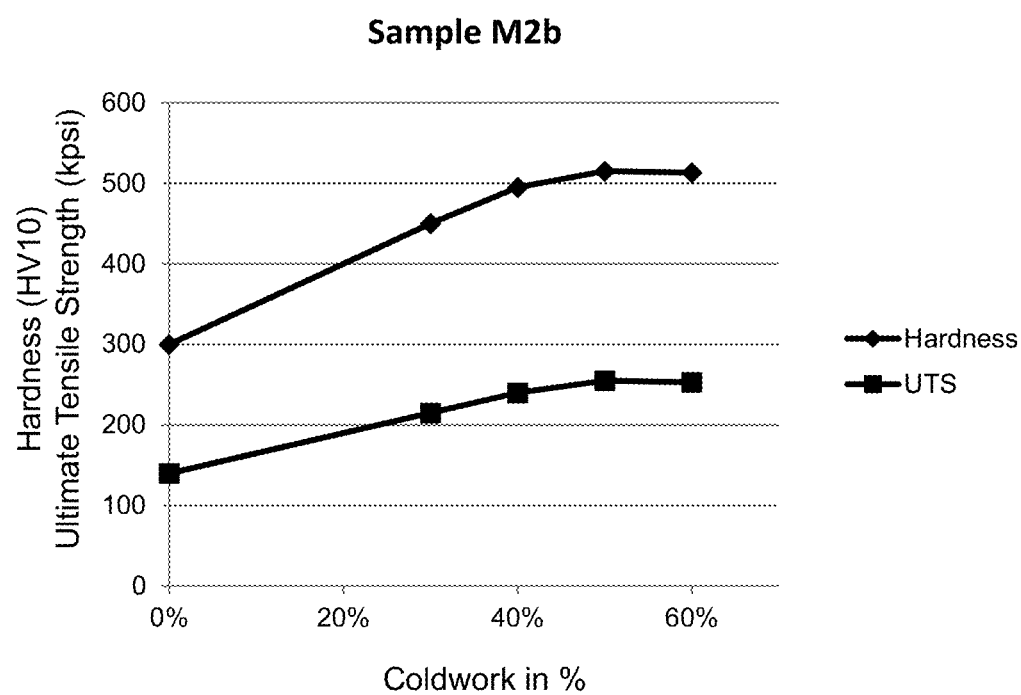
Figure 5:
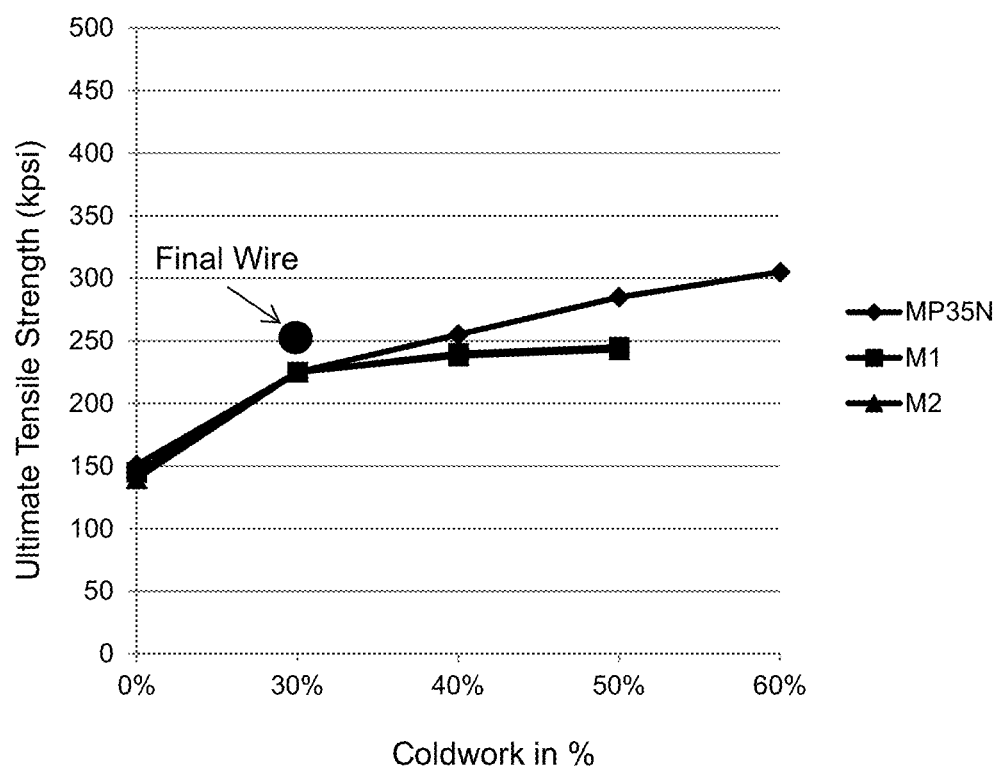
FIG. 5 compares Co-based alloys/wires in accordance with various embodiments of the invention with commercially available Co-based alloys in ultimate tensile strength (UTS)

FIGS. 3 and 4 depict mechanical properties, hardness (HV) and ultimate tensile strength (UTS) vs. coldwork % (dislocation strengthening), for wires using samples M1b and M2b in Table V, wherein M1b forms the entire wire and M2b is used as an outer shell around a core of tantalum (Ta) to form a composite wire. FIG. 5 compares UTS of the wire with sample alloy M1b having about 20.1 wt % Pt (also see FIG. 3); with the composite wire having an outer shell of sample alloy M2b having about 19.5 wt % Pt (also see FIG. 4); and commercial MP35N LT alloy having no dense metal member Pt, but other similar metal elements as compared with the alloy samples M1b and M2b.

As illustrated in FIGS. 3-5, wires that include alloy M1b and alloy M2b/Ta surprisingly have similar ultimate tension strength (UTS) mechanical properties as compared with a wire that includes the conventional MP35N LT alloy. As further indicated in FIG. 5, a "final wire" data point indicates the desired coldwork % and UTS in the final material.

Table VI further lists dimensions, mechanical properties of sample alloys M1b and M2b having an alloy composition listed in Table V.

TABLE VI

Wires Having Co-based Alloys including Ni

| | M1b Wire | M2b/Ta Composite Wire |
|---|---|---|
| Diameter | 0.087 mm (0.0034 inch) | 0.087 mm (0.0034 inch) |
| Length | 30.000 mm (1.1811 inch) | 50.000 mm (1.9685 inch) |
| Yield strength | 1900 MPa (277 kpsi) | 1090 MPa (159 kpsi) |
| UTS | 2200 MPa (321 kpsi) | 1150 MPa (168 kpsi) |
| Elongation | 4.1% | 0.3% |

Radiopaque Properties

In general, radiography relies on differences in the density of materials being imaged to provide an image contrast between materials. This is because relatively high density materials absorb greater amounts of radiation than low density materials. The relative thickness of each material normal to the path of the radiation also affects the amount of radiation absorbed. For placing stents in smaller vessel lumens, it is desirable to use a stent having a relatively thin cross section or wall thickness, which in turn makes stents of known material less radiopaque and difficult to position in a body lumen. For this reason, the disclosed Co-based alloys are desired at least for providing improved radiopaque properties.

Radiopaque properties of alloys were characterized by calculating mass absorption coefficient of the alloy material. The higher the calculated mass absorption coefficient, the better the radiopacity. For example, theoretical alloy density may be calculated according to the equation:

$$\frac{1}{\rho_{alloy}} = \sum_i \left(\frac{w_i}{\rho_i}\right),$$

while the theoretical mass absorption coefficient may be calculated according to the equation:

$$(\mu/\rho)_{alloy} = \sum_i w_i (\mu/\rho)_i,$$

where $w_i$ is the weight percent of the $i^{th}$ alloying element; $\mu$ is the linear absorption coefficient of the material; $\mu/\rho$ is the mass absorption coefficient; and $(\mu/\rho)_i$ is the mass absorption coefficient for the $i^{th}$ alloying element in the pure state. The mass absorption coefficient, $\mu/\rho$, is constant for a given material and energy of incident radiation.

According to the equations discussed above, Table VII lists calculated and actual density as well as calculated mass absorption coefficient of the alloy sample M1b and the conventional alloy MP35N having compositions shown in Table V at 80 keV and 100 keV, which are in the realm of current C-arm equipment for cardiology.

TABLE VII

| Alloys | Calculated Density (g/cm³) | Actual Density (g/cm³) | Calculated Mass Absorption Coefficient (cm²/g) at | |
|---|---|---|---|---|
| | | | 80 keV | 100 keV |
| M1b | 9.87 | — | 2.694 | 1.558 |
| MP35N | 8.54 | 8.43 | 0.774 | 0.466 |

As indicated in Table VII, at both 80 keV and 100 keV, the sample alloy M1b containing dense metal member Pt has a calculated mass absorption coefficient higher than the corresponding commercially available alloy MP35N. The sample alloy M1b provides better radiopaque properties over MP35N.

Example 6

Stents were fabricated with composite wires having an outer diameter of about 0.0032". The composite wires had a core-shell structure with an outer shell formed of the commercially available MP35N, while the inner core having (1) about 25% Ta, (2) about 41% Ta, (3) about 25% $Pt_{20}Ir$, and (4) about 41% $Pt_{20}Ir$ by weight, all of which are compared with a control group manufactured from a solid MP35N alloy. The composite wires were melted or alloyed at the end of the stents.

Corrosion studies were performed on the above four exemplary wires. The effects of alloying between materials, and their percentages used for the outer shell and the inner core were examined on the corrosion resistance of the stents. No further processing was conducted to passivate or alter the surface chemistry of the stents.

As a result, the PtIr core, when melted at the end of the stent, had no effect on (i.e., maintained) the stent's ability to self-passivate regardless of the percentage used, when compared to the control group. In other words, the Co-based alloys composed of constituents from MP35N/35NLT and $Pt_{20}Ir$ result in a corrosion resistance material at least equivalent to the commercially available MP35N. On the other hand, both tantalum (Ta) groups showed a lack of repassivation when compared to the control samples. The percentage of tantalum (Ta) also had an effect, illustrated by the 41% Ta core group, which was not fully repassivated.

Example 7

Figure 6:
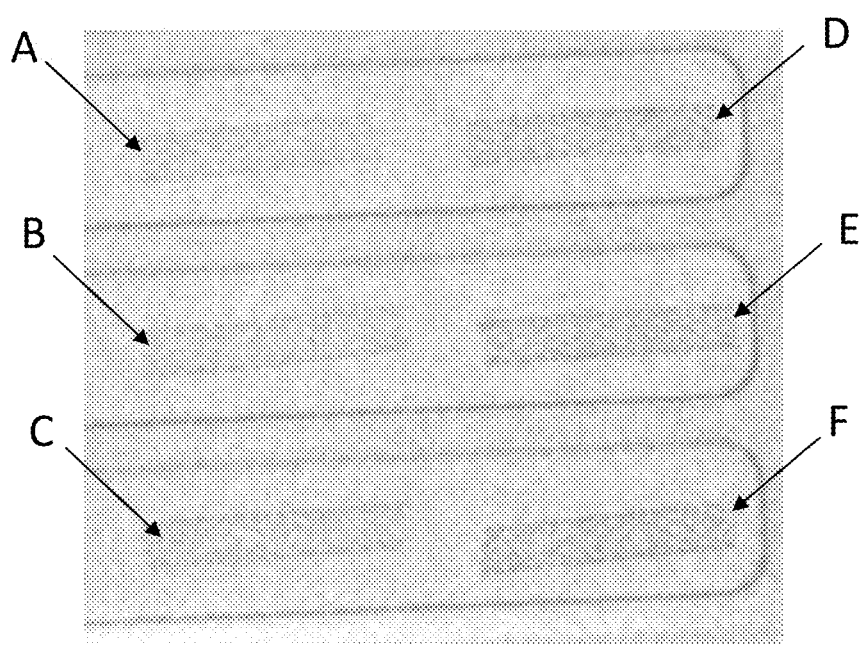
FIG. 6 illustrates differences in radiopacity of stents made from a commercial Co-based alloy and stent made from alloys in accordance with embodiments of the invention.

Identical stents were made from wires having three different thicknesses, including 0.0032 inches (sample A), 0.0034 inches (sample B), and 0.0036 inches (sample C), formed from MP35N LT. In addition, stents were made from wires in accordance with embodiments of the invention, including a wire having a thickness of 0.0036 inches formed from an alloy comprising about 35.2 weight % Co, about 20.1 weight % Pt, about 16.8 weight % Cr, about 17.2 weight % Ni, and about 11.1 weight % Mo (sample D), a wire having a thickness of 0.0034 inches formed from an alloy comprising about 37 weight % Fe, about 30.8 weight % Pt, about 18.4 weight % Cr, about 9.5 weight % Ni, and about 1.5 weight % Mo (sample E), and a wire having a thickness of 0.0033 inches formed from an alloy comprising about 37.1 weight % Ni, about 21 weight % Pt, about 17.7 weight % Cr, about 13.3 weight % W, about 4.9 weight % Co, about 4.4 weight % Fe, and about 2.2 weight % Mo (sample F). The stents were placed in a tray and put under a standard C-arm/fluoroscope used in hospital catheter labs. A layer of lead shielding was placed over the tray to add background noise and illustrate radiopacity differences between the materials, as illustrated in FIG. 6. As illustrated, samples D, E, and F, which all include platinum (Pt), showed a higher level of radiopacity than samples A, B, and C, which were formed from commercially available MP35N LT, which does not include platinum.

More specifically, sample D, which is a wire having a thickness of 0.0036 inches that was formed from an alloy comprising about 35.2 weight % Co, about 20.1 weight % Pt, about 16.8 weight % Cr, about 17.2 weight % Ni, and about 11.1 weight % Mo, showed a higher level of radiopacity than a wire of the same thickness that was formed from a commercial MP35N LT alloy. As noted above with respect to Example 5, a wire that was formed from an alloy comprising about 35.2 weight % Co, about 20.1 weight % Pt, about 16.8 weight % Cr, about 17.2 weight % Ni, and about 11.1 weight % Mo had surprisingly similar UTS when compared to a wire that was formed from a commercial MP35N LT alloy. The results provided in Examples 5 and 7 show that a novel cobalt based alloy with platinum results in an improvement in radiopacity of a stent, while retaining mechanical properties of the stent, as compared to commercially available cobalt based alloys, such as MP35N LT.

Example 8

It was desirable to show that the materials in accordance with embodiments of the invention can maintain the appropriate ductility/elongation in the material compared to MP35N, which is an alloy that is commonly used in the manufacture of stents, in view of the amount of strain that the stent material undergoes during its lifecycle (i.e. during crimping, deployment, and loading). In addition, it was desirable to determine the appropriate level of annealing to maximize the ductility in the material, while balancing strength. In this example, wires made from the M1b sample listed in Table V having a diameter of 0.091 mm (0.0036 inches) were tested for mechanical properties after being annealed at different temperatures (850° C., 950° C., 1000° C., and 1050° C.) for different times (6 seconds, 12 seconds, 24 seconds, 30 seconds, 36 seconds, and 42 seconds) and were compared to wires made from MP35N, in accordance with ASTM F562, after being annealed at the same temperatures (850° C., 950° C., 1000° C., and 1050° C.) for different times (6 seconds, 12 seconds, 24 seconds, and 30 seconds).

Figure 7A:
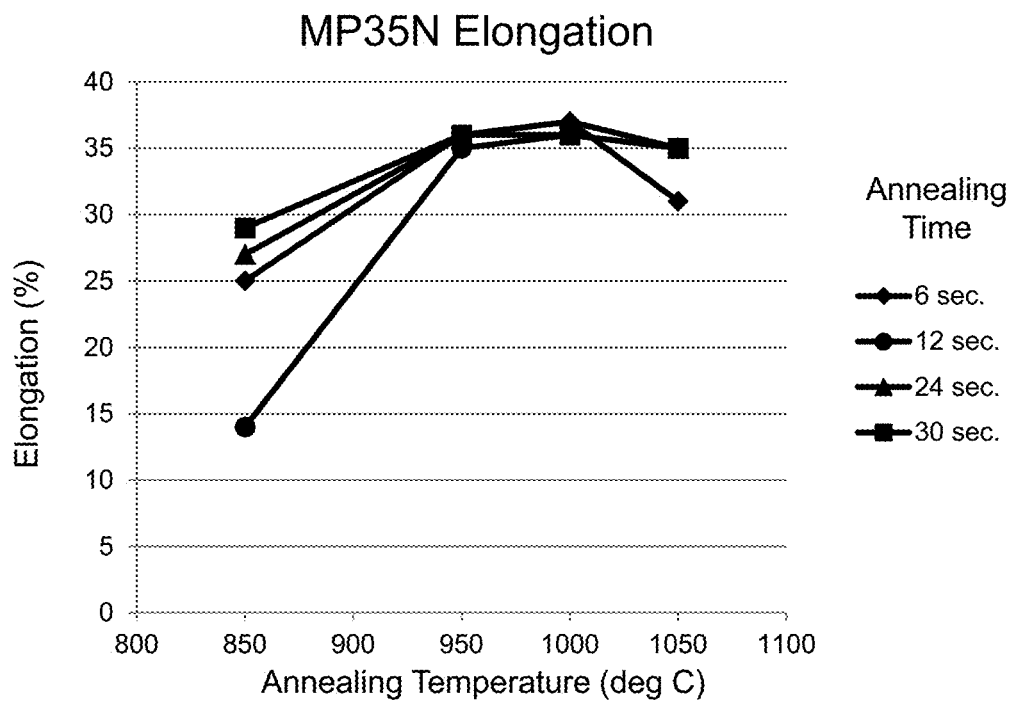
FIGS. 7A and 7B compare the elongation of wires made from a Co-based alloy in accordance with an embodiment of the invention to wires made from a commercial material used to manufacture stents as a function of annealing temperature and annealing time.
Figure 7B:
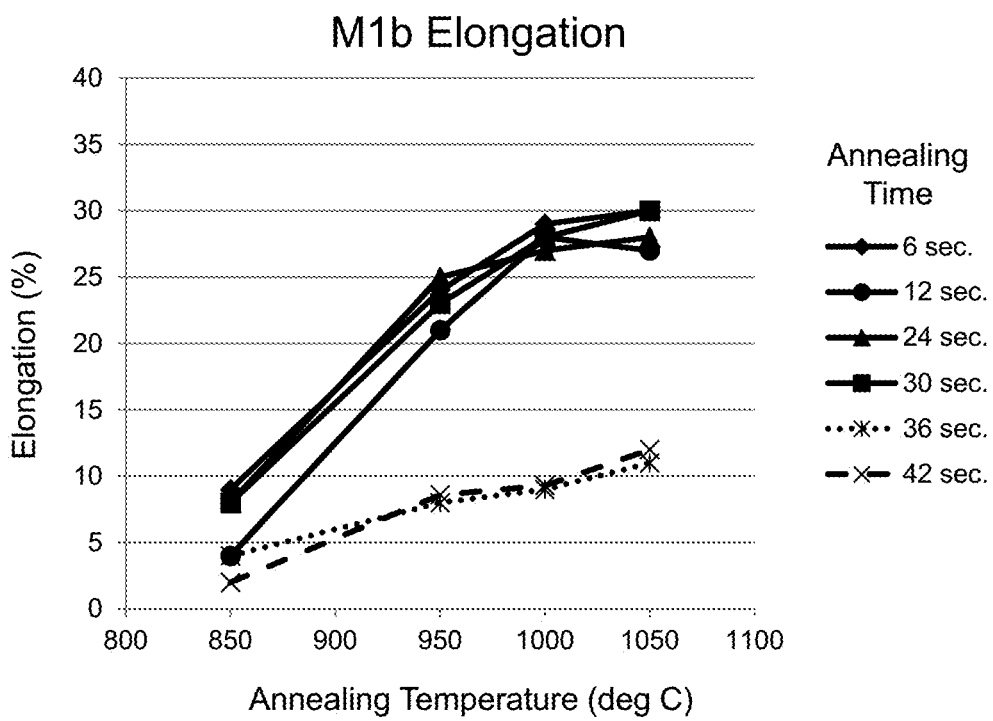
Figure 8A:
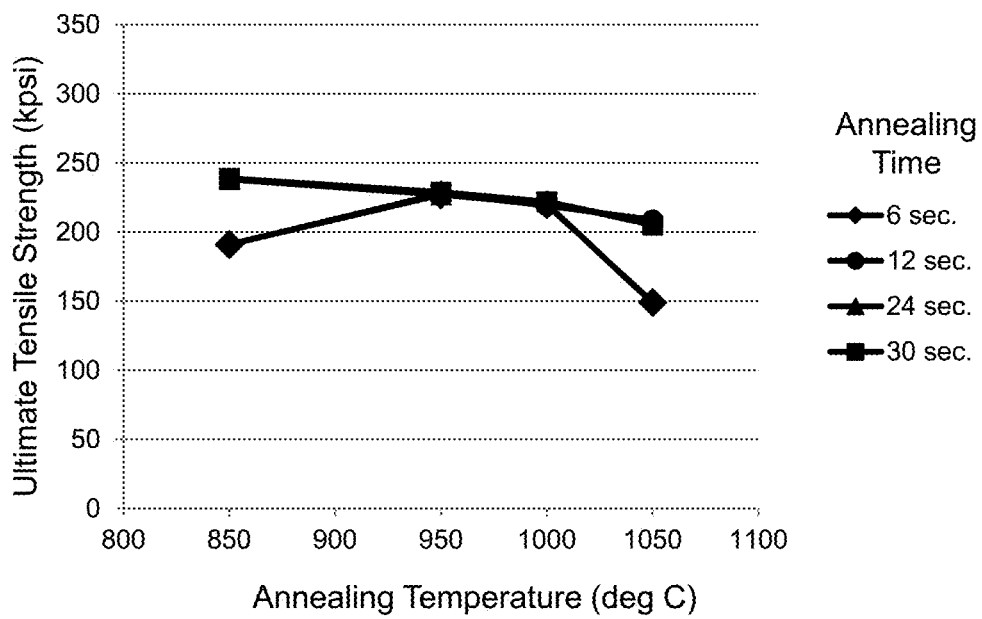
FIGS. 8A and 8B compare the ultimate tensile strengths of the wires made from a Co-based alloy in accordance with an embodiment of the invention to wires made from a commercial material used to manufacture stents as a function of annealing temperature and annealing time.
Figure 8B:
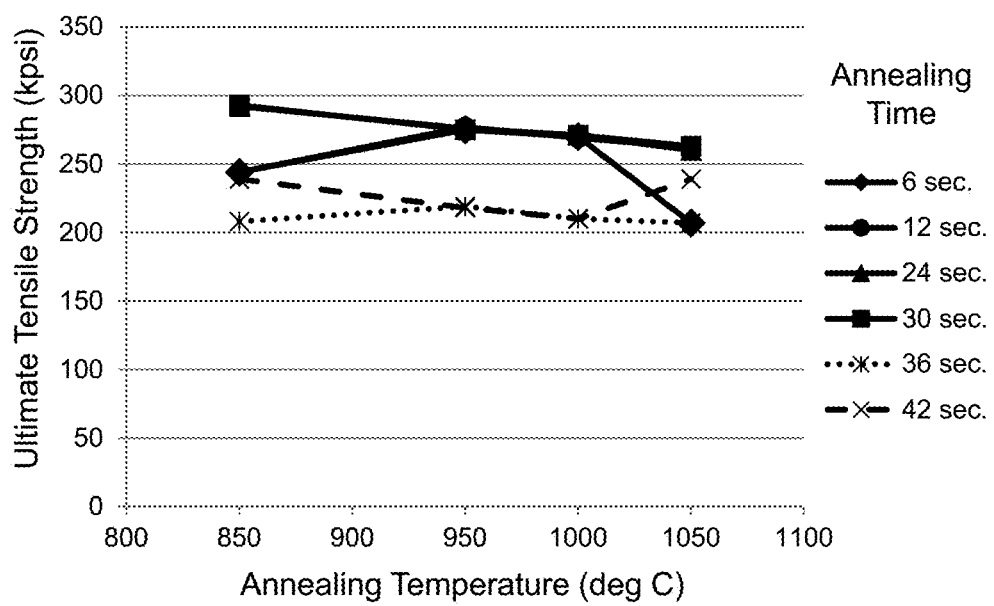
Figure 9A:
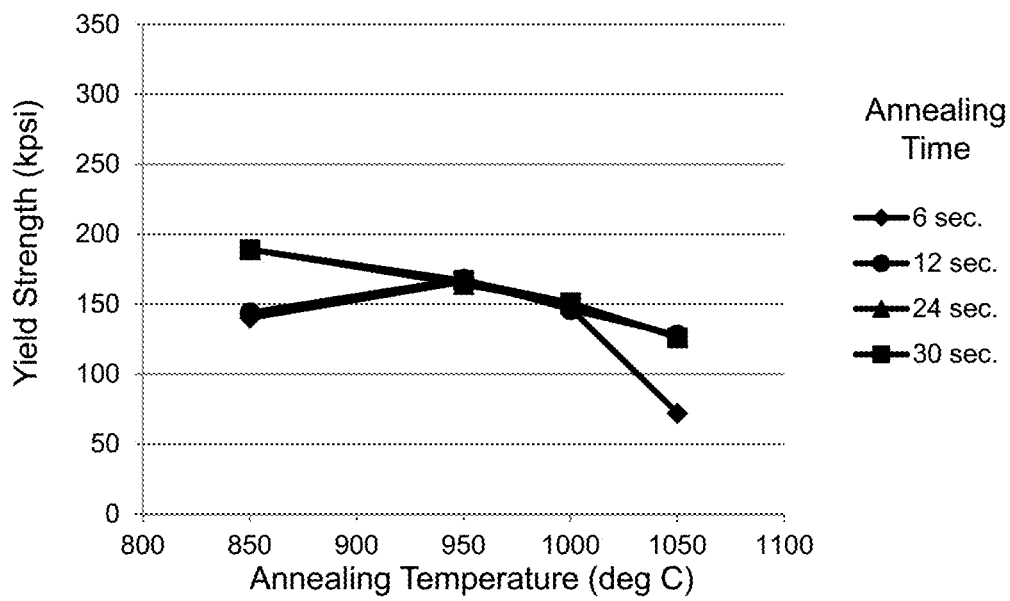
FIGS. 9A and 9B compare the yield strengths of the wires made from a Co-based alloy in accordance with an embodiment of the invention to wires made from a commercial material used to manufacture stents as a function of annealing temperature and annealing time.
Figure 9B:
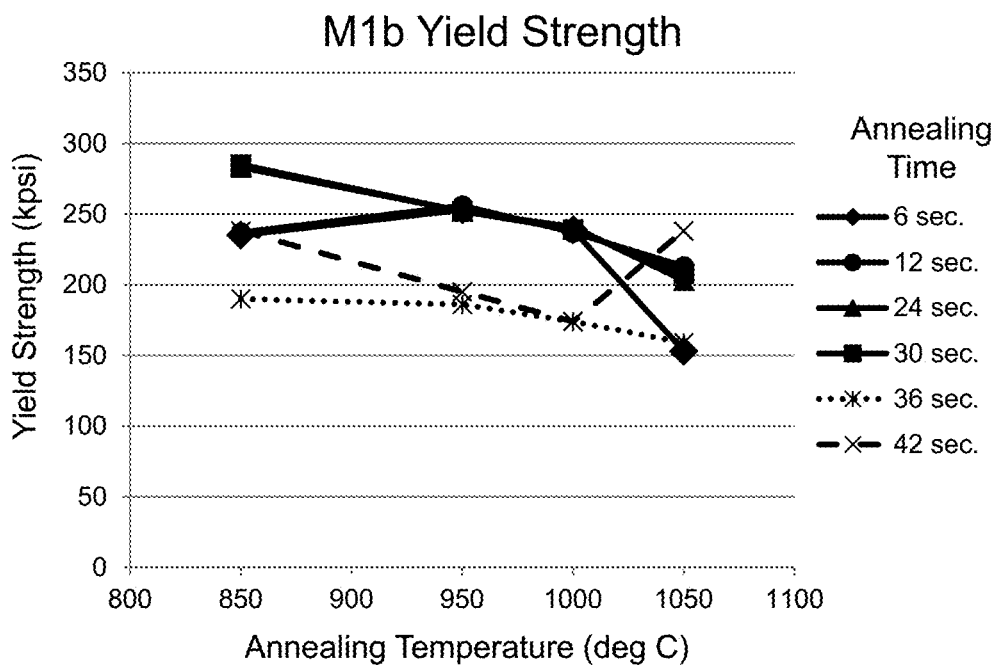

FIG. 7A illustrates the percent elongation that was measured for the wires made from the MP35N alloy as a function of annealing temperature and annealing time, and FIG. 7B illustrates the percent elongation that was measured for the wires made from the M1b alloy sample as a function of annealing temperature and annealing time. FIG. 8A illustrates the ultimate tensile strength (in kpsi) that was measured for the wires of FIG. 7A as a function of annealing temperature and annealing time, and FIG. 8B illustrates the ultimate tensile strength (in kpsi) that was measured for the wires of FIG. 8B as a function of annealing temperature and annealing time. FIGS. 9A and 9B, illustrate the yield strength (in kpsi) that was measured for the wires of FIGS. 7A and 7B, respectively, as a function of annealing temperature and annealing time.

As illustrated, the M1b alloy was able to achieve a ~30% elongation, which indicates the material should have ample ductility for undergoing the strains associated with a stent material during the lifecycle of the stent, after being annealed at 1050° C. In comparison, the MP35N alloy achieved a ~35% elongation. In addition, the ultimate tensile strength of the M1b alloy was generally higher than the ultimate tensile strength of the MP35N alloy for comparable annealing temperatures and times, as illustrated by FIGS. 8A and 8B. Similar results were also found for yield strength, as illustrated in FIGS. 9A and 9B. The testing results indicate that although the ductility of the M1b alloy was lower than the ductility of the MP35N alloy, the M1b alloy is generally a stronger material, as evidenced by the ultimate tensile strength and yield strength that were measured for the wire samples, and appropriate for manufacturing stents.

The wire samples of M1b alloy and MP35N were also tested for Vickers hardness with a test load of 100 g for 10 seconds. The M1b alloy sample with no annealing was measured to have a Vickers hardness of 602. Table VIII lists the results of the Vickers hardness test (hardness values in HV) as a function of annealing temperature and time.

TABLE VIII

Vickers Hardness Test Results

| | Time | | | | | | | |
|---|---|---|---|---|---|---|---|---|
| | 6 sec. | | 12 sec. | | 24 sec. | | 30 sec. | |
| Temp. | MP35N | M1b | MP35N | M1b | MP35N | M1b | MP35N | M1b |
| 850° C. | 354 | 531 | 425 | 537 | 500 | 534 | 380 | 528 |
| 950° C. | 325 | 481 | 326 | 476 | 321 | 489 | 335 | 486 |
| 1000° C. | 303 | 452 | | 456 | 308 | 459 | 312 | 449 |
| 1050° C. | 279 | 418 | 273 | 452 | 267 | 420 | 279 | 429 |

As shown in Table VIII, the M1b alloys were tested to be slightly harder than the MP35N alloy for comparable annealing temperatures and times.

Although stents are described herein, the alloys according to embodiments of the invention may be used for any number of implantable medical devices.

While specific embodiments of the invention have been described above, it will be appreciated that the invention may be practiced otherwise than as described. For example, Tables I and II include additional Examples that were not described in detail, but still fall within the present invention and are claimed below. The descriptions above are intended to be illustrative, not limiting. For example, although the alloys are described as being used to make a stent, it should be appreciated that other medical devices may also be fabricated with such alloys in accordance with embodiments of the invention. Thus, it will be apparent to one skilled in the art that modifications may be made to the invention as described without departing from the scope of the claims set out below.

What is claimed is:

1. A stent comprising:
a cobalt-based alloy, wherein the cobalt-based alloy is free of molybdenum (Mo), the cobalt based alloy comprising
about 14 weight % tungsten (W) and 10-14 weight % platinum (Pt);
20-24 weight % chromium (Cr);
8-12 weight % nickel (Ni);
0-3 weight % iron (Fe); and
balance cobalt (Co).

2. The stent of claim 1, wherein the cobalt-based alloy is free of molybdenum (Mo) and is formed of:
about 14 weight % tungsten (W) and 10-14 weight % platinum (Pt);
about 22 weight % chromium (Cr);
8-12 weight % nickel (Ni)
0-0.15 weight % carbon (C);
0-3 weight % iron (Fe);
about 1.5 weight % manganese (Mn);
0-1.0 weight % silicon (Si);
0-0.03 weight % lanthanum (La); and
balance cobalt (Co).

3. A stent comprising:
a plurality of struts formed by a wire, the wire comprising an outer shell substantially surrounding an inner core, wherein one of the outer shell and the inner core comprises a cobalt-based alloy and the other of the outer shell and the inner core comprises a metal member selected from the group consisting of platinum (Pt), gold (Au), iridium (Ir), osmium (Os), rhenium (Re), tungsten (W), palladium (Pd), tantalum (Ta), and combinations thereof, the cobalt-based alloy comprising:
10-35 weight % the metal member;
16-21 weight % chromium (Cr);
9-12 weight % molybdenum (Mo);
10-18 weight % nickel (Ni);
0-3 weight % iron (Fe); and
balance cobalt (Co).

4. The stent of claim 3, wherein the metal member of the cobalt-based alloy and the metal member of the other of the outer shall and the inner core comprises about 20% to and 45% by weight of the total wire comprising the outer shell and the inner core.

5. The stent of claim 3, wherein the cobalt-chromium alloy comprises about 1 weight % iron (Fe).

6. A stent comprising:
a cobalt-based alloy comprising
10-35 weight % metal member selected from the group consisting of platinum (Pt), gold (Au), iridium (Ir), osmium (Os), rhenium (Re), tungsten (W), palladium (Pd), tantalum (Ta), and combinations thereof;
16-21 weight % chromium (Cr);
9-12 weight % molybdenum (Mo);
10-18 weight % nickel (Ni);
0-3 weight % iron (Fe); and
balance cobalt (Co).

7. The stent of claim 6, wherein the cobalt-chromium alloy comprises about 1 weight % iron (Fe).

8. The stent of claim 6, wherein the cobalt-based alloy further comprises one or more of
0-0.015 weight % boron (B);
0-0.15 weight % carbon (C);
0-1.5 weight % manganese (Mn);

0-0.04 weight % phosphorous (P);
0-1.0 weight % silicon (Si);
0-1 weight % titanium (Ti); and
0-0.03 weight % sulfur (S).

9. The stent of claim 6, wherein the cobalt-based alloy further comprises one or more of
  about 0.010 weight % boron (B);
  0-0.025 weight % carbon (C);
  0-1.0 weight % iron (Fe);
  0-0.15 weight % manganese (Mn);
  0-0.015 weight % phosphorous (P);
  0-0.15 weight % silicon (Si);
  0-0.01 weight % sulfur (S); and
  0-1 weight % titanium (Ti).

* * * * *